(12) United States Patent
Seo et al.

(10) Patent No.: US 12,728,067 B2
(45) Date of Patent: Sep. 8, 2026

(54) MASSAGE APPARATUS INCLUDING OSCILLATORS

(71) Applicant: CERAGEM CO., LTD., Chungcheongnam-do (KR)

(72) Inventors: Yong Seob Seo, Chungcheongnam-do (KR); Sang Ho Choi, Chungcheongnam-do (KR); Jae Hwa Kim, Chungcheongnam-do (KR); Dong Myoung Lee, Chungcheongnam-do (KR); Yong Son Park, Chungcheongnam-do (KR)

(73) Assignee: CERAGEM CO., LTD., Chungcheongnam-Do (KR)

( * ) Notice: Subject to any disclaimer, the term of this patent is extended or adjusted under 35 U.S.C. 154(b) by 401 days.

(21) Appl. No.: 16/108,467

(22) Filed: Aug. 22, 2018

(65) Prior Publication Data

US 2019/0060159 A1 Feb. 28, 2019

(30) Foreign Application Priority Data

Aug. 22, 2017 (KR) ........................ 10-2017-0106062

(51) Int. Cl.
*A61H 11/00* (2006.01)
*A61F 7/00* (2006.01)
(Continued)

(52) U.S. Cl.
CPC .............. *A61H 11/00* (2013.01); *A61F 7/007* (2013.01); *A61H 23/0254* (2013.01);
(Continued)

(58) Field of Classification Search
CPC .......... A61H 2205/08; A61H 2205/083; A61H 2201/165; A61H 2201/1628–163;
(Continued)

(56) References Cited

U.S. PATENT DOCUMENTS 4,559,929 A * 12/1985 Hseu .................. A61H 23/0263 366/111
5,140,976 A 8/1992 Cheng
(Continued)

FOREIGN PATENT DOCUMENTS

CN 203425225 U * 2/2014
CN 110151516 8/2019
(Continued)

OTHER PUBLICATIONS

KR200293766(Y1) machined translation obtained, Dec. 31, 2020 (Year: 2020).*

(Continued)

*Primary Examiner* — Paige Kathleen Bugg
(74) *Attorney, Agent, or Firm* — NORTON ROSE FULBRIGHT US LLP

(57) ABSTRACT

Disclosed is a massage apparatus including oscillators which receive supplied power and oscillate under control of a controller. Here, two oscillators installed to allow oscillation directions thereof to be at right angle are included, and the controller sequentially controls power supplied to the two oscillators to perform oscillations in an order of a bowel movement direction.

6 Claims, 6 Drawing Sheets

(51) Int. Cl.
*A61H 23/02* (2006.01)
*A61H 39/04* (2006.01)

(52) U.S. Cl.
CPC ......... *A61H 23/0263* (2013.01); *A61H 39/04* (2013.01); *A61F 2007/0022* (2013.01); *A61F 2007/0077* (2013.01); *A61H 2201/0153* (2013.01); *A61H 2201/0207* (2013.01); *A61H 2201/0228* (2013.01); *A61H 2201/1215* (2013.01); *A61H 2201/1454* (2013.01); *A61H 2201/165* (2013.01); *A61H 2201/1654* (2013.01); *A61H 2201/169* (2013.01); *A61H 2201/50* (2013.01); *A61H 2201/5002* (2013.01); *A61H 2205/083* (2013.01)

(58) Field of Classification Search
CPC .............. A61H 11/00; A61H 2011/005; A61H 23/00–06; A61H 23/0254; A61H 23/0263; A61H 2201/0153; A61H 2201/0207; A61H 2201/0228; A61H 2201/1215; A61H 2201/1454; A61H 2201/1654; A61H 2201/169; A61H 2201/50; A61H 2201/5002; A61F 7/007
USPC ........................................................... 601/93
See application file for complete search history.

(56) References Cited

U.S. PATENT DOCUMENTS

| | | | | |
|---|---|---|---|---|
| 6,217,533 | B1 * | 4/2001 | McCambridge ... | A61H 23/0263<br>601/56 |
| 2002/0068886 | A1 * | 6/2002 | Lin ..................... | A61H 9/0078<br>601/15 |
| 2005/0059909 | A1 * | 3/2005 | Burgess .................. | A61F 7/007<br>601/15 |
| 2006/0241534 | A1 * | 10/2006 | Tsai ...................... | A61H 7/001<br>601/15 |
| 2007/0167885 | A1 * | 7/2007 | Moon .................... | A61H 11/00<br>601/71 |
| 2015/0011921 | A1 * | 1/2015 | Sidhu ..................... | A61H 39/04<br>601/134 |
| 2017/0119620 | A1 * | 5/2017 | Trapp ................. | A61H 23/0263 |

FOREIGN PATENT DOCUMENTS

| | | | | |
|---|---|---|---|---|
| JP | H05123372 | | 5/1993 | |
| JP | 2005013543 | | 1/2005 | |
| JP | 3131720 | | 5/2007 | |
| KR | 20-0111324 | | 4/1993 | |
| KR | 10-2001-0105134 | | 11/2001 | |
| KR | 200293766 | | 11/2002 | |
| KR | 200307181 | Y1 * | 3/2003 | ............ A61H 39/04 |
| KR | 10-2005-0094935 | | 9/2005 | |
| KR | 10-0538044 | | 12/2005 | |
| KR | 10-2009-0098112 | | 9/2009 | |
| KR | 10-0920239 | | 10/2009 | |
| KR | 10-2012-0052563 | | 5/2012 | |
| KR | 200293766 | Y1 * | 11/2012 | |
| RU | 2153314 | | 7/2000 | |
| RU | 2192840 | | 11/2002 | |
| RU | 119611 | | 8/2012 | |
| RU | 175014 | | 11/2017 | |
| WO | WO-2017042599 | A1 * | 3/2017 | ............ A61H 7/007 |

OTHER PUBLICATIONS

CN-203425225-U machined translation obtained, Dec. 31, 2020 (Year: 2020).*

Professional Physical Therapy. "Bowel Health and Abdominal Massage Treatment for Constipation", Nov. 15, 2021. Accessed at <https://www.professionalpt.com/bowel-health-and-abdominal-massage-treatment-for-constipation-blog/> on May 30, 2023. (Year: 2021).*

Translation of KR-200307181 (Year: 2003).*

Notice of Allowance issued in Corresponding Russian Application No. 2020108326, dated Jul. 29, 2020.

Office Action issued in Corresponding Japanese Application No. 2020-511380, dated Mar. 16, 2021 (English Translation provided).

International Search Report issued in Corresponding PCT Application No. PCT/KR2018/004145, dated Jul. 13, 2018 (English Translation).

Office Action issued in Corresponding Chinese Application No. 201711286563.1, dated Jun. 3, 2020 (English Translation provided).

Extended European Search Report Issued in Corresponding European Patent Application No. 18848361.4, dated Apr. 21, 2021.

Office Action Issued in Corresponding Chinese Patent Application No. 201711286563.1, dated May 19, 2021.

* cited by examiner

MASSAGE APPARATUS INCLUDING OSCILLATORS

CROSS-REFERENCE TO RELATED APPLICATION

This application claims priority to and the benefit of Korean Patent Application No. 2017-0106062, filed on Aug. 22, 2017, the disclosure of which is incorporated herein by reference in its entirety.

BACKGROUND

1. Field of the Invention

The present invention relates to a massage apparatus including oscillators, and more particularly, to a massage apparatus including oscillators alternately installed in a perpendicular direction.

2. Discussion of Related Art

Massage is one kind of physical therapy which gives a physical stimulus to skin or a body part to stimulate the corresponding body part for treating a disease or improving health. Generally, the corresponding body part is pressurized by hands or a certain apparatus to stimulate blood vessels or a response point such that blood circulation is promoted, knotted muscles are loosened, or fat is broken down, similar to an effect of dieting.

Although massage has generally been performed using a force of hands, recently, many massage apparatuses have been developed such that massage using a massage apparatus is commonly performed.

A variety of such massage apparatuses are available according to a size or a method of use, and among them, small user-friendly portable massage apparatuses are available.

Small-sized massage apparatuses are driven while being in contact with a body part desired by a user to intensively massage only the corresponding body part, and a variety of such apparatuses are present in related art. As examples thereof, Patent Documents 1 to 4 are present.

Patent Document 1 discloses a belt-typed rotary vibration sporting goods including a support member; a controller located in a center of a front surface of the support member and configured to include a control switch and an acupressure gear assembly; a thermal acupressure portion located in a center of a rear surface of the support member; and a pair of vibrating portions located on both sides of the controller, wherein the thermal acupressure portion includes a plurality of thermal balls, a thermal ball printed circuit board for controlling a temperature of the thermal balls, and first and second thermal printed circuit board for driving the thermal balls, wherein the pair of vibrating portions include a motor, a first vibrating gear mounted on the motor, a second vibrating gear connected to the first vibrating gear by a timing belt and configured to drive a vibrating cam, and vibration-proof rubbers located above the second vibrating gear and below the vibrating cam.

Patent Document 2 discloses an ultrasonic belt including a belt body formed by cutting out two or more pieces of cloth, artificial leather, or the like to have a width and length capable of adequately surrounding the waist and abdominal region of a human body and sewing a circumference thereof; elastic bandages fixedly sewed to both ends of the belt body to provide the waist and abdominal region with pressure when being worn; and adhesive bandages sewed to one sides of ends of the elastic bandages to maintain the belt in a state of surrounding the waist and abdominal region of the human body, wherein several ultrasonic oscillators are arranged at intervals in a lateral direction in the belt body and sequentially or randomly operated at certain time intervals by a controller installed outside the belt body such that fat present in the abdominal region and the like may be broken down through thermal vibrations of ultrasonic waves to suppress abdominal obesity and the like and blood circulation may be promoted to speed up metabolism.

Patent Document 3 discloses a low frequency vibrating heat stimulation apparatus including a belt on which a mounting portion in contact with the abdominal region of a user is formed; a plurality of low frequency stimulating ceramics configured to generate low frequencies on an inner surface of the belt; thermally conductive washers provided at bottom ends of the low frequency stimulating ceramics to surround the low frequency stimulating ceramics; a printed circuit board on which the plurality of low frequency stimulating ceramics and the thermally conductive washers corresponding to the low frequency stimulating ceramics are mounted; a heating body provided for a thermal stimulus through the inner surface of the belt; a thermally conductive panel provided to conduct heat generated by the heating body through the printed circuit board to increase a temperature; a vibration motor mounted in a center of a rear surface of the printed circuit board for a vibrating stimulus; a vibration motor cover which surrounds an outside of the vibration motor; a controller which controls the low frequency stimulating ceramics, the heating body, and the vibration motor; and an output line through which a signal controlled by the controller is transmitted to the belt.

Patent Document 4 discloses a machine for curing constipation and shedding weight from an abdominal region, which is driven by a micro computer and has contracting and projecting acupressure protrusions. The machine includes a waist belt including a circular-plate-shaped body and an adhesive fastening portion extending from left and right sides of the body and coming in contact with the abdominal region and fastening the body to the waist. The body includes a front body portion formed on a front surface and a rear body portion installed on a rear surface of the front body portion. The front body portion includes a liquid crystal panel portion formed on top, a plurality of program operation buttons installed below the liquid crystal panel portion, a power switch installed on one side below the plurality of program operation buttons, and an alternating current/direct current (AC/DC) conversion adapter insertion hole installed on one side surface of one of the program operation buttons to supply power. Also, the rear body portion includes nine contracting and projecting acupressure protrusions having oscillators operated according to the principle of solenoid and heating wires installed in a cross shape among the nine contracting and projecting acupressure protrusions.

Although some of the above-described conventional massage apparatuses include a plurality of oscillators and have a function of adjusting oscillation directions of the oscillators, the oscillation directions are limited to inward and outward or frontward and rearward directions such that oscillations of the oscillators may interfere with bowel movements or does not provide any help thereto when the abdominal region is massaged.

SUMMARY OF THE INVENTION

The present invention is directed to allowing an order of oscillations of oscillators to help and not to interfere in a bowel movement.

According to an aspect of the present invention, there is provided a massage apparatus including oscillators which receive supplied power and oscillate under control of a controller. Here, two oscillators installed to allow oscillation directions thereof to be at right angle are included, and the controller sequentially controls power supplied to the two oscillators to allow oscillations to be performed in an order of a bowel movement direction.

The oscillators may each include an eccentric oscillating body having a semicircular-cylindrical shape and a motor configured to rotate a rotating shaft of the eccentric oscillating body.

The massage apparatus may further include a plurality of ceramics fixed by skin foam to a front surface of a support plate with the oscillators installed on a rear surface thereof.

The massage apparatus may further include a heating plate installed between the support plate and the skin foam.

The massage apparatus may further include handle holes formed on both ends of the massage apparatus to be easily gripped with hands.

The massage apparatus may further include belt fixing holes to or from which a wearing belt is attached or detached and which are formed on both end walls of the massage apparatus.

According to another aspect of the present invention, there is provided a massage apparatus including oscillators which receive supplied power and oscillate under control of a controller. Here, three oscillators installed to allow oscillation directions thereof to be at 60 degrees are included, and the controller sequentially controls power supplied to the three oscillators to allow oscillations to be performed in an order of a bowel movement direction.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
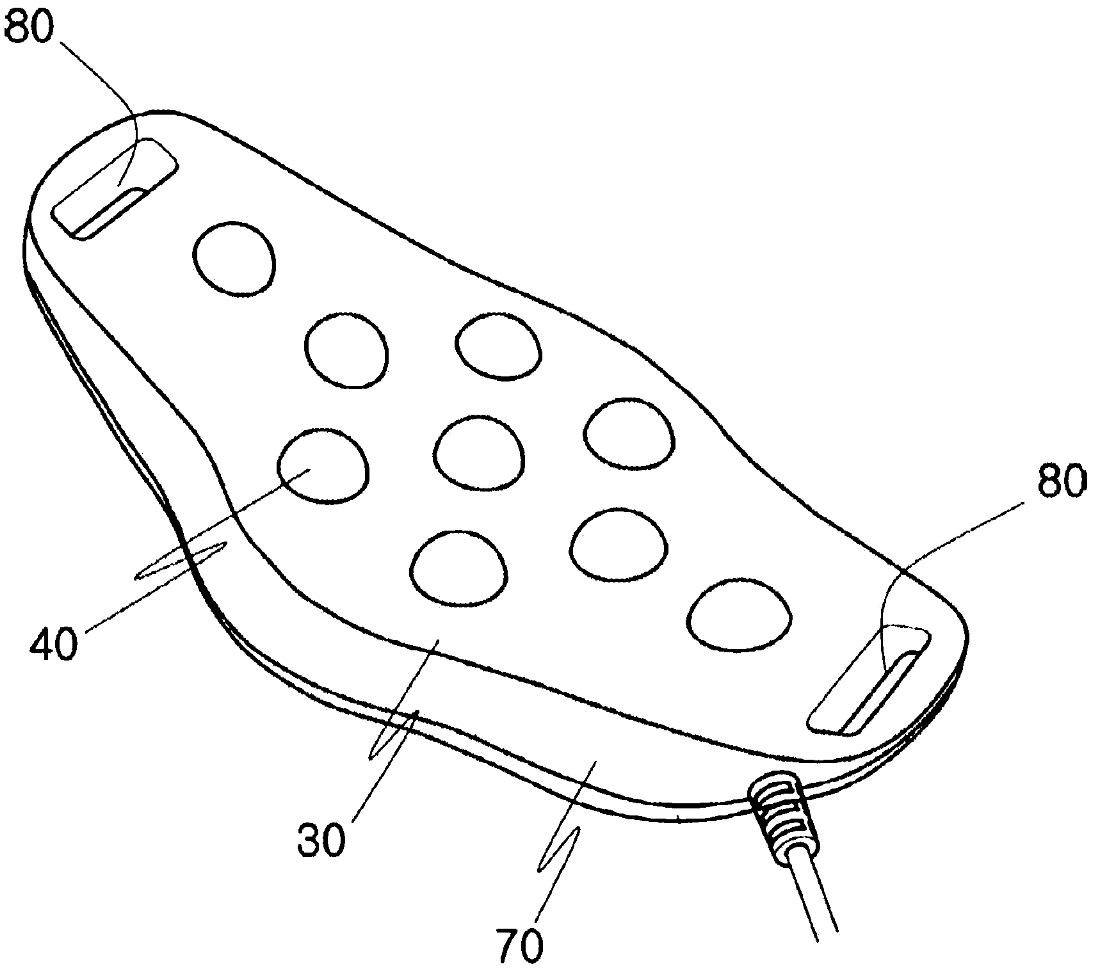
FIG. 1 is a perspective view illustrating an example of a massage apparatus including alternately installed oscillators in a perpendicular direction according to one embodiment of the present invention.

Since the present invention may be variously changed and may have a variety of embodiments, exemplary embodiments will be described herein in detail with reference to the drawings. However, it should be understood that the present invention is not limited to the exemplary embodiments and includes all changes and equivalents or substitutes included in the concept and technical scope of the present invention.

Throughout the drawings, like reference numerals refer to like elements. In the description of the embodiments of the present invention, a detailed description of a well-known technology of the related art will be omitted when it is deemed to obscure the essence of the present invention.

The present invention may facilitate a bowel movement by oscillators which oscillate in an order according to a bowel movement direction.

In a massage apparatus according to one embodiment of the present invention, two oscillators 10 may be perpendicularly arranged to each other to hit (oscillate) in different directions. That is, when the two oscillators are perpendicularly arranged to each other, one may hit in leftward and rightward directions and another may hit in upward and downward directions. Here, when an order of four hits (hits in the upward, downward, leftward, and rightward directions) is controlled, a hitting order (an oscillation order) may be performed according to a bowel movement direction (clockwise when viewed in front of a user).

The oscillators 10 may be controlled by a controller (not shown), and the controller may control the oscillation order of the oscillators 10 by controlling power supplied to the oscillators 10.

Figure 3:
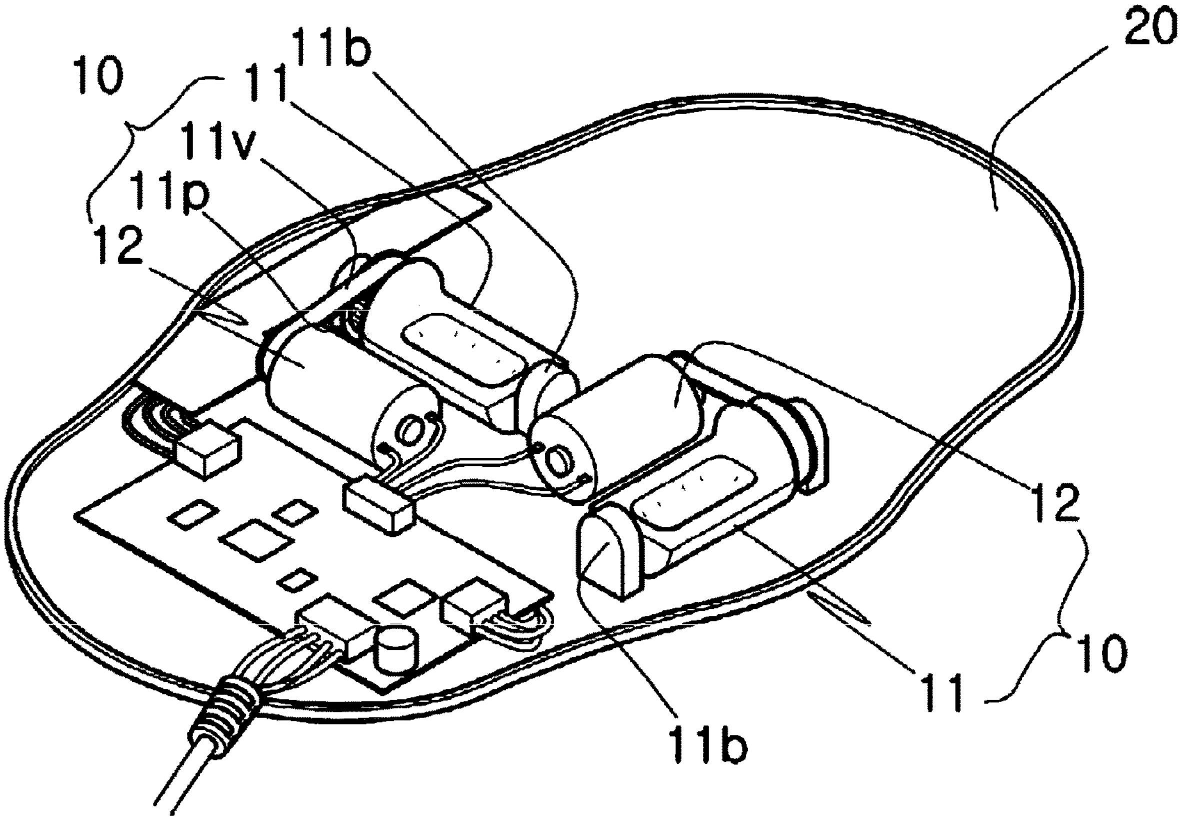
FIG. 3 is a perspective view illustrating oscillator-installation parts which form the massage apparatus including alternately installed oscillators in the perpendicular direction according to one embodiment of the present invention.
Figure 4:
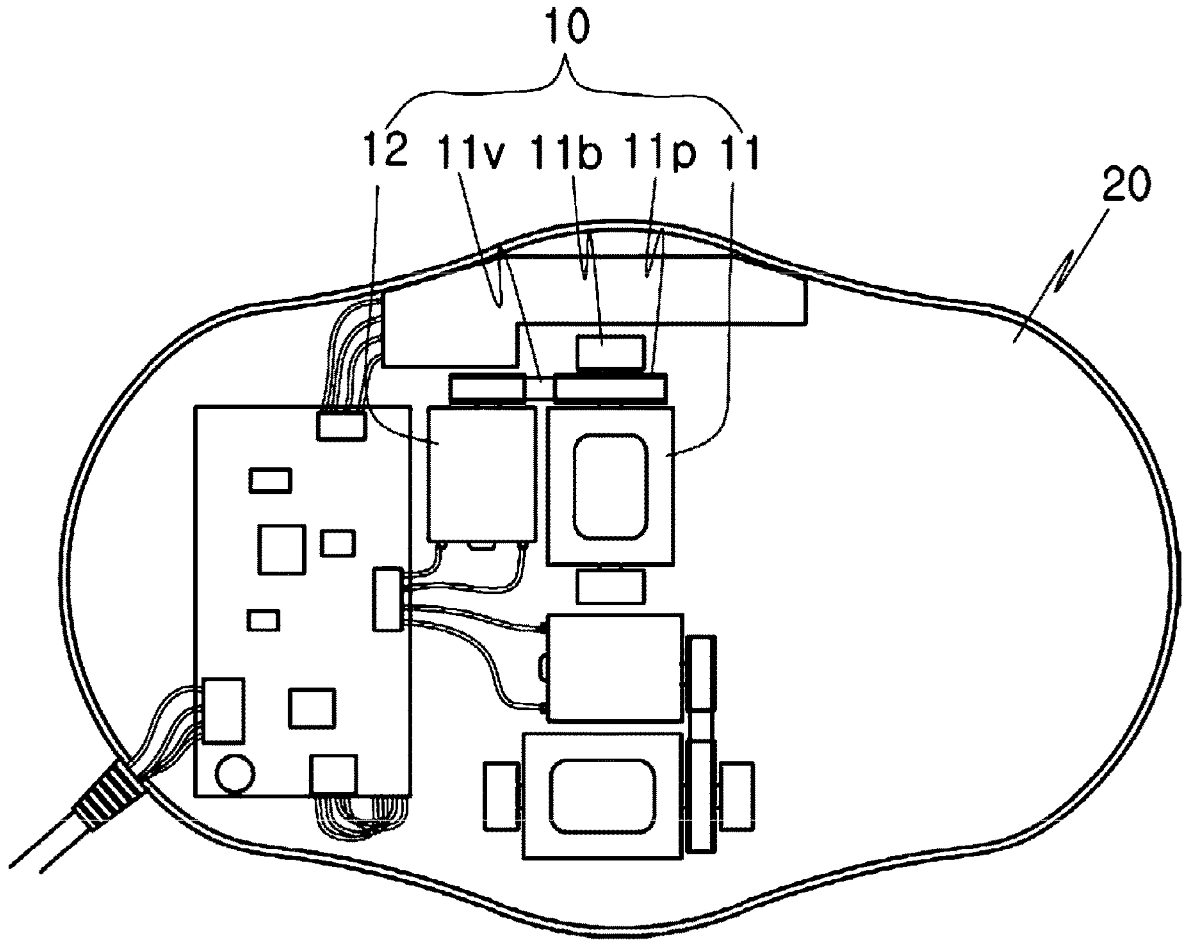
FIG. 4 is a plan view illustrating an oscillator arrangement state of the massage apparatus including alternately installed oscillators in the perpendicular direction according to one embodiment of the present invention.

In the massage apparatus according to one embodiment of the present invention, the oscillation order of the oscillators 10 may be controlled by the controller controlling the power supplied to the oscillators 10 and the oscillators 10 are arranged on a rear surface of a support plate 20 to perpendicularly alternate with each other as shown in FIGS. 3 and 4.

The oscillators 10 may be implemented with various modifications. However, according to an exemplary example, as shown in FIGS. 3 and 5, each of the oscillators 10 includes an eccentric oscillating body 11 configured to have a semicircular-cylindrical shape and include an eccentric rotating shaft 11*s* and a motor 12 which rotates the rotating shaft 11*s* of the eccentric oscillating body 11.

Figure 5:
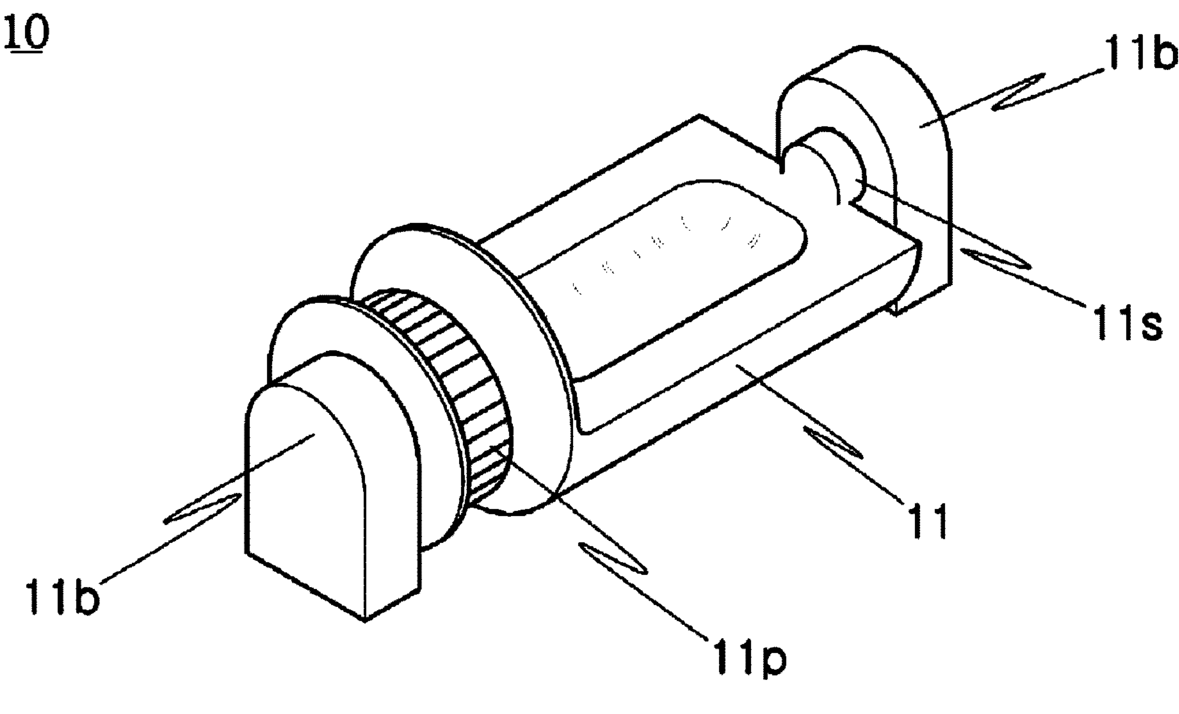
FIG. 5 is a perspective view illustrating an eccentric oscillating body installed in the massage apparatus according to one embodiment of the present invention.

The eccentric oscillating body 11, as shown in an enlarged view in FIG. 5, has a semicircular cylinder shape and includes the rotating shaft 11*s* formed to be eccentric to one side such that the eccentric oscillating body 11 at a position eccentric from the rotating shaft 11*s* applies a force to the rear surface of the support plate 20 to oscillate when being rotated by a rotational force of the motor 12.

To transfer power of the motor 12, which forms part of the oscillator 10, to the eccentric oscillating body 11, pulleys 11*p* are installed at one end of the eccentric oscillating body 11 and a motor shaft and a belt 11*v* is installed between the pulleys 11*p* to transfer the power of the motor 12 to the eccentric oscillating body 11.

Bearings 11*b* support both ends of the eccentric oscillating body 11 in order to rotatably support the rotating shaft 11*s* of the eccentric oscillating body 11.

Although the eccentric oscillating body 11 may repeat rotating in leftward and rightward rotations or may rotate in any one direction, a preferable rotational direction is to allow a direction of the order of hits (oscillations) applied to the user to be the same as a bowel movement direction (a movement direction of digestive organs).

The present invention may facilitate a bowel movement by oscillating the oscillators 10 in the order according to the bowel movement direction.

The massage apparatus according to one embodiment of the present invention may further include a variety of functions similar to a general massage apparatus.

When a thermal function is added to the massage apparatus according to one embodiment of the present invention, the bowel movement may be more stimulated to redouble effects.

To perform the thermal function, ceramics 40 and a heating plate 50 are included.

Figure 2:
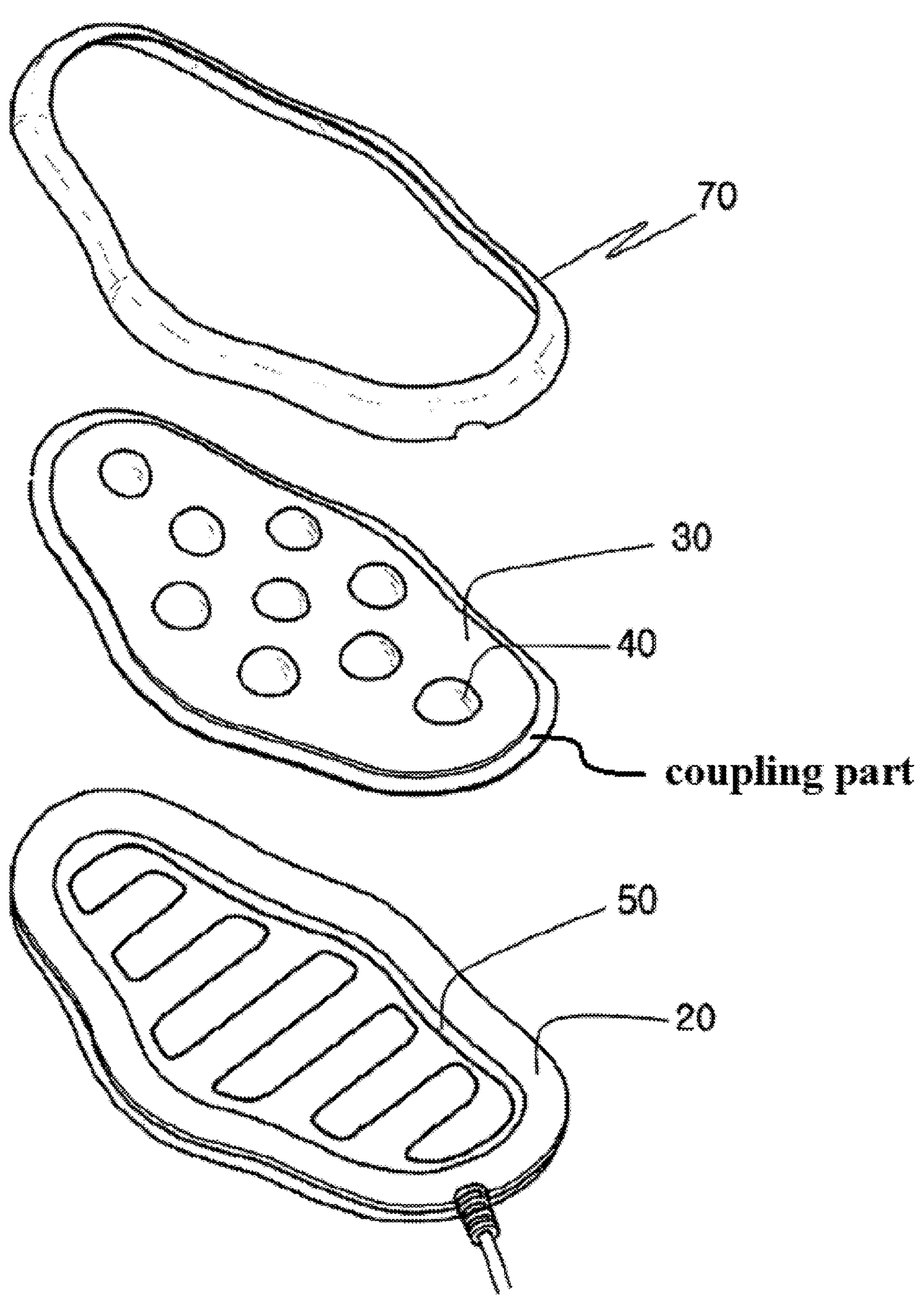
FIG. 2 is an exploded perspective view illustrating the example of the massage apparatus including alternately installed oscillators in the perpendicular direction according to one embodiment of the present invention.
Figure 6:
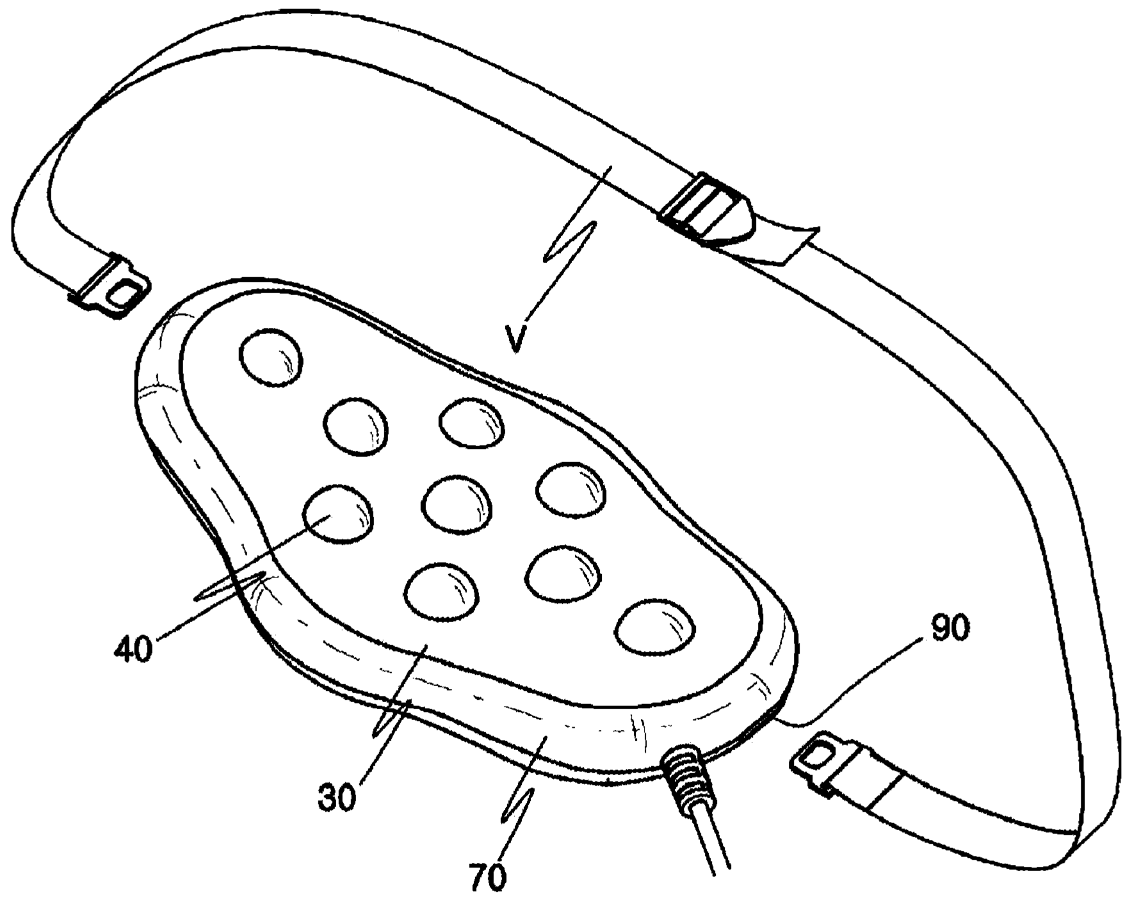
FIG. 6 is a perspective view illustrating another example of the massage apparatus including alternately installed oscillators in the perpendicular direction according to one embodiment of the present invention.

The ceramics 40 are parts for effectively applying oscillations of the oscillators 10 to a human body, include spherical ends toward the outside of the massage apparatus as shown in FIGS. 1, 2, and 6, and are formed of a material having excellent heat conductivity.

The ceramics 40 are installed to allow inner ends to come into surface contact with a front surface of the support plate 20 on which the oscillators 10 are installed such that oscillations of the oscillators 10 are transferred to the ceramics 40 through the support plate 20.

The heating plate 50 is further installed between the ceramics 40 and the support plate 20.

The heating plate 50 is a part for enhancing a massage effect by generating heat and heating a massaged part of the human body which is formed by tortuously arranging heating wires in a zigzag shape or a meandering shape as shown in FIG. 2, and is fixed to the front surface of the support plate 20. The heating wires may be replaced by an aluminum heating body, non-woven carbon fabric, a cotton mesh heating body, a carbon fabric heating body, and the like.

The ceramics 40 are installed to come into direct contact with the front surface of the heating plate 50 such that heat of the heating plate 50 may be supplied to the human body through the ceramics 40. Skin foam 30 is installed as a supporting part for supporting the inner ends of the ceramics 40 to come into contact with the heating plate 50.

The skin foam 30 according to one embodiment of the present invention is formed of an elastic material such as integral skin foam. However, the skin foam 30 may be replaced by an elastic material (for example, rubber and the like) in addition to the integral skin foam. Here, the skin foam 30 may be referred to as a buffering fixing portion.

Also, the massage apparatus according to one embodiment of the present invention may be used while being directly gripped by hands of the user or being worn on the body of the user.

To use the massage apparatus while gripping with hands, handle holes 80 are formed in both ends of the massage apparatus to be gripped by hands as shown in FIG. 1. To use the massage apparatus while wearing on the body, belt fixing holes 90 to or from which a wearing belt V is attached or detached may be formed in both end walls of the massage apparatus as shown in FIG. 6.

For gripping or wearing according to a selection of the user, both the handle holes 80 and the belt fixing holes 90 may be formed. Also, both the handle holes 80 and the belt fixing holes 90 may be omitted.

In the massage apparatus configured as described above, a rear cover is detachably installed on the rear surface of the support plate 20 to easily install the oscillators 10 and oscillator-driving circuits on the rear surface of the support plate 20, the skin foam 30 is fixed to an edge of the support plate 20, and a support edge 70 is installed to cover a coupling part between the skin foam 30 and the support plate 20.

Although the two oscillators installed to allow oscillation directions thereof to be at right angle are included in the above embodiment, three oscillators installed to allow oscillation directions thereof to be at 60 degrees may be included.

Here, hits (oscillations) may be applied in six directions, not four directions. Here, power supplied to oscillators is sequentially controlled by a controller such that oscillations may be performed in an order of a bowel movement direction.

Also, four oscillators installed to allow oscillation directions thereof to be at 45 degrees may be included.

The assembling structure may be embodied in a variety of modifications and detailed descriptions thereof will be omitted.

According to the embodiments of the present invention, a massage apparatus allows oscillations to be sequentially performed in a direction of a bowel movement such that an effect of stimulating the bowel movement using the massage apparatus is provided.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. A massage apparatus comprising:

a plurality of ceramics;

a heating plate supporting the plurality of ceramics; and at least two oscillators configured to receive supplied power and oscillate under control of a controller, wherein the at least two oscillators are installed to allow oscillation directions thereof to be at a right angle, and the controller is configured to sequentially control power supplied to the at least two oscillators, wherein each of the at least two oscillators comprise an eccentric oscillating body having a semicircular-cylindrical shape and a motor configured to rotate a rotating shaft of the eccentric oscillating body, wherein a first oscillator of the at least two oscillators is configured to oscillate in a leftward direction and in a rightward direction, and a second oscillator of the at least two oscillators is configured to oscillate in an upward direction and in a downward direction, wherein the plurality of ceramics are supported to allow inner ends of the plurality of ceramics to come into direct surface contact with a front surface of the heating plate, wherein the heating plate is installed on a front surface of a support plate, wherein the plurality of ceramics are fixed by a buffering fixing portion to the front surface of the support plate, wherein a supporting edge is a separate component from the heating plate and the support plate, and is configured to cover a coupling part between the buffering fixing portion and an edge of the support plate, and wherein the at least two oscillators are installed on a rear surface of the support plate.

2. The massage apparatus of claim 1, wherein the buffering fixing portion comprises skin foam.

3. The massage apparatus of claim 2, wherein the heating plate is installed between the support plate and the buffering fixing portion.

4. The massage apparatus of claim 3, further comprising handle holes formed on both ends of the massage apparatus configured to be gripped by a user's hands.

5. The massage apparatus of claim 3, further comprising belt fixing holes to or from which a wearing belt is attached or detached and which are formed on both end walls of the massage apparatus.

6. The massage apparatus of claim 1, wherein the controller is configured to sequentially control the at least two oscillators by sequentially moving (i) the first oscillator in the rightward direction, (ii) then the second oscillator in the downward direction, (iii) then the first oscillator in the leftward direction, and (iv) then the second oscillator in the upward direction to perform oscillations in an order of a bowel movement direction.

* * * * *